United States Patent [19]

Wagner, Jr.

[11] Patent Number: 4,772,791
[45] Date of Patent: Sep. 20, 1988

[54] NEURORECEPTOR ACTIVITY ASSESSMENT

[75] Inventor: Henry N. Wagner, Jr., Baltimore, Md.

[73] Assignee: Johns Hopkins University, Baltimore, Md.

[21] Appl. No.: 28,396

[22] Filed: Mar. 20, 1987

Related U.S. Application Data

[62] Division of Ser. No. 715,371, Mar. 25, 1985.

[51] Int. Cl.⁴ ............................................. G01T 1/167
[52] U.S. Cl. .................................. 250/363 S; 250/369
[58] Field of Search .................... 250/363 SF, 363 SA, 250/363 SR, 369

[56] References Cited

U.S. PATENT DOCUMENTS 3,781,557  12/1973  Carugati et al. ............... 250/363 SF

OTHER PUBLICATIONS

Stephen E. Derenzo, "Detectors, Sampling, Shielding, and Electronics For Positron Emission Tomography", *Donner Laboratory and Lawrence Berkeley Laboratory* Document No. LBL-13091 University of California, Berkeley, California (Aug. 1981), pp. 1-6.

Charles A. Burnham, Saul Aronow, and Gordon L. Brownell, "A Hybrid Positron Scanner", *Phys. Med. Biol.*, vol. 15, No. 3, (Jul. 1970), pp. 517-528.

In re Chandler, 117, USPQ, pp. 361-65.

Primary Examiner—Janice A. Howell
Assistant Examiner—Constantine Hannaher
Attorney, Agent, or Firm—Cushman, Darby & Cushman

[57] ABSTRACT

The effectiveness of drugs and substances that affect brain chemistry can be efficiently and relatively inexpensively monitored. Radioactive tracer substances comprising a ligand that binds to presynaptic or postsynaptic neuroreceptors is administered to a patient. Emissions (primarily positrons, and gamma rays which are emitted from the positrons) are measured. These emissions are indicative of the number and the degree of occupancy or blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs is based upon the comparisons made. Dopamine, serotonin, opiate, and other receptors all may be monitored, and the procedures are particularly applicable to treatment of Parkinson's disease, schizophenia, and drug addictions. Simple apparatus is utilized including a patient head support and first and second gamma ray directional detectors (such as NaI or BiGe detectors) disposed on opposite sides of the head support, and connected to circuitry including photomultiplier tubes, preamplifiers, and circuitry for correcting for random gamma ray detections.

3 Claims, 2 Drawing Sheets

NEURORECEPTOR ACTIVITY ASSESSMENT

This is a division of application Ser. No. 715,371 filed Mar. 25, 1985.

BACKGROUND AND SUMMARY OF THE INVENTION

For the treatment of a wide variety of different nervous and mental diseases, and drug addictions, it is desirable to be able to effectively (both from the technological and cost standpoints) monitor the effectiveness of drugs and substances that affect brain chemistry. For instance in the treatment of schizophrenia, it is highly desirable to be able to gauge the brain biochemical effects of a dose of a neuroleptic drug (such Haloperidol) administered for blocking the patient's dopamine receptors, since if too little of the drug is administered the desired blockade does not occur, and if too much of the drug is administered there are severe side effects. Since less than one percent of the administered drug is bound by the neuroreceptors, it is difficult to determine by analysis of bodily fluids and discharges, and the like, how effective the treatment is for a particular patient. Similarly, in the treatment of drug addicts as, for example, in a methadone treatment program, it is desirable to obtain the optimum dosage for a given patient as quickly as possible, and if withdrawal symptoms occur, to change dosage as necessary.

According to the present invention, a method and apparatus are provided which provide for technological and cost-effective monitoring of the effectiveness of drugs and substances that affect brain chemistry so that the dosage of drugs affecting brain chemistry (such as in the treatment of nervous and mental disorders, and drug addiction) can be optimized. The invention has wide applicability, being applicable to dopamine, serotonin, opiate, and other neuroreceptors, can utilize a wide variety of radioactive tracer substances, such as carbon 11, fluorine 18, nitrogen 13, and oxygen 15, and can utilize a wide variety of apparatus.

According to the present invention, the most inexpensive, yet effective, apparatus is only a fraction of the cost of a positron-emission tomography (PET) scanner, and can detect microcurie doses of radiation, as opposed to millicurie doses that are needed for PET scanners. The preferred apparatus comprises a support structure for supporting a patient in a supine position, including a head support. First and second gamma ray directional detectors, such as NaI or BiGe detectors, are provided and are mounted so that one is operatively positioned on either side of the patient's head when supported by the head support. Lead collinators, or the like, may be provided to limit the field of view of the detectors. Circuitry means are operatively connected to the detectors for measuring the number of gamma rays detected thereby, the circuitry means typically including a photo multiplier tube and preamplifier operatively connected to each detector, and circuitry means for correcting for random gamma rays detected by the detectors.

According to one aspect of the invention, there is provided a method of optimizing the effect on a living patient of drugs and substances that affect brain chemistry, comprising the steps of: (a) Administering to the patient a tracer substance comprising or consisting of a ligand that binds to presynaptic or postsynaptic neuroreceptors. (b) Waiting a period of time sufficient for the ligand to bind to the neuroreceptors. (c) Measuring emissions from the tracer substance which are indicative of the number of the patient's neuroreceptors and the degree of occupancy or blocking of the patient's neuroreceptors. (d) Calculating the number of neuroreceptors and the degree of occupancy or blocking of the neuroreceptors utilizing a mathematical model computation. (e) Comparing the calculations obtained in step (d) with an intra-person control, if one is available for the patient, or if an intra-person control for the patient is not available, comparing the calculations with an inter-person control, to determine the degree of drug response. And, (f) gauging further treatment of the patient with drugs or substances that affect brain chemistry based upon the comparison made in step (e). The method is applicable to the treatment of schizophrenia, Parkinson's disease, focal epilepsy, tardive dyskinesia, Huntington's disease, and other nervous and mental disorders, and also can be applied to the treatment of drug addictions, as by determining the optimum dosage of methadone to prevent withdrawal, and in the administration of drugs for blocking opiate neuroreceptors (such as Naltrexone).

According to another, specific, aspect of the invention there is provided a method of monitoring the effectiveness of dopamine neuroreceptor blockage of a living schizophrenic patient, comprising the steps of: (a) Administering to the patient a radioactive dopamine receptor blocking drug. (b) Measuring radioactive emissions from the radioactive drug from the time of injection until some predetermined time thereafter, the pre-determined time being related to the half life of the radioactive element in the drug administered. (c) After the radioactive tracer drug has substantially disappeared by radioactive decay, administering to the patient a predetermined dose of dopamine neuroreceptor blocking drug in non-radioactive form. (d) Repeating step (a). (e) Repeating step (b). And, (f) determining the degree of blockade of the dopamine neuroreceptors utilizing the predetermined dose administered in step (c), by comparing the measurements obtained in steps (b) and (e).

According to still another specific aspect of the present invention, there is provided a method of monitoring the effectiveness of the treatment of drug addiction of a patient comprising the steps of: (a) Administering to the patient a radioactive opiate receptor blocking drug. (b) Measuring radioactive emissions from the radioactive drug from the time of injection until some predetermined time thereafter, the pre-determined time being related to the half life of the radioactive element in the drug administered. (c) After the radioactive tracer drug has substantially disappeared by radioactive decay, administering to the patient a predetermined dose of opiate neuroreceptor blocking drug in non-radioactive form. (d) Repeating step (a). (e) Repeating step (b). And, (f) determining the degree of blockade of the opiate neuroreceptors utilizing the predetermined dose administered in step (c), by comparing the measurements obtained in steps (b) and (e).

It is the primary object of the present invention to provide for the effective monitoring of the effect of drugs and substances on brain chemistry. This and other objects of invention will become clear from an inspection of the detailed description of the invention, and from the appended claims.

DETAILED DESCRIPTION OF THE DRAWINGS

Figure 1:
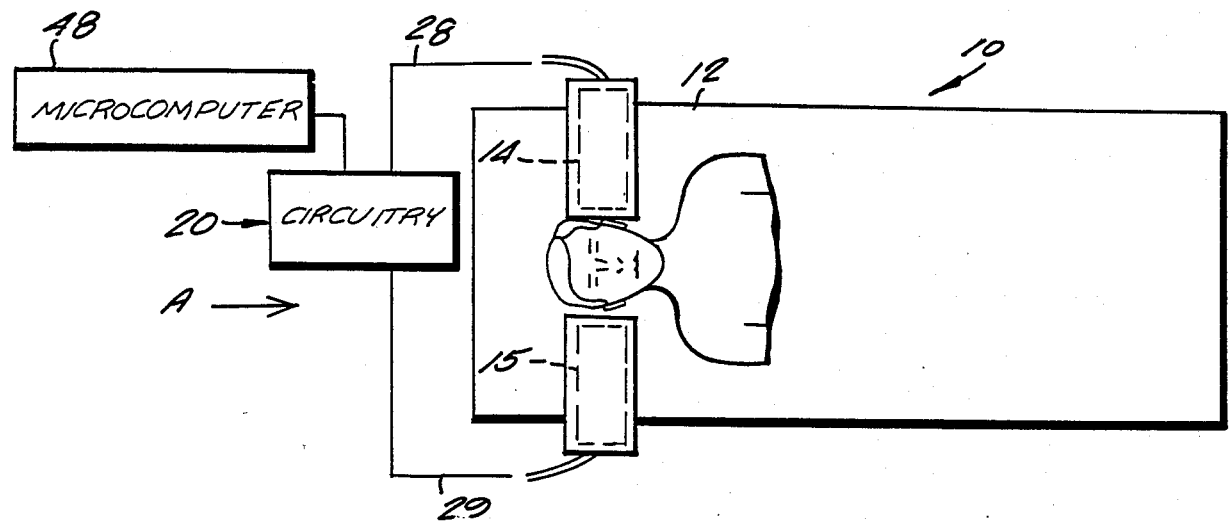
FIG. 1 is a top schematic view of exemplary apparatus according to the present invention.

Exemplary preferred apparatus according to the present invention is illustrated schematically generally by reference numeral 10 in FIG. 1. The basic components of the apparatus include the patient support structure 12, first and second directional gamma ray detectors 14 and 15, means, shown generally by reference numerals 16 and 17, for mounting the detectors 14, 15, and circuitry means, shown generally by reference numeral 20.

The patient support structure 12 comprises a stretcher, slab, or other support structure for supporting a patient (as illustrated schematically in FIGS. 1 and 2) in a generally supine position. The support structure 12 includes a head support structure 22 (see FIG. 2) adapted to support the patient's head.

The gamma ray directional detectors may be selected from a variety of gamma ray detectors. In the exemplary embodiment illustrated in FIG. 3, the detectors are shown as sodium iodide (NaI) detectors, but may include bismith germanate (BiGe) detectors, or even conventional gamma counters alone if collimated (to directionate them). The detectors 14, 15 typically will detect positron emissions since positrons emitted from radioactive tracers within the patient's head travel one or two mm within the brain and then combine with an electron to yield two gamma rays that come off in opposite directions through the skull.

Figure 2:
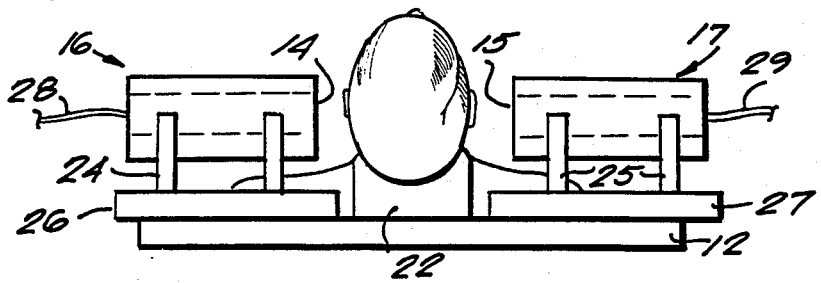
FIG. 2 is an end view, looking in the direction of arrow A of FIG. 1, of the apparatus of FIG. 1.

In the exemplary embodiment illustrated in FIGS. 1 and 2, the means 16, 17 for mounting and limiting the field of view of the detectors 14, 15, mount the detectors so that they are operatively disposed on opposite sides of the patient's head, preferably in line with each other and generally concentric with a line passing through the patient's ears. The structures 16, 17 comprise lead collimators, with the detectors 14, 15 disposed within the interior bores of the collimators. The collimators are mounted by U-shaped brackets 24, 25, or the like to plates 26, 27, or the like (such as plastic (e.g. "Lucite") plates), which in turn rest upon the patient support structure 12 as illustrated in FIGS. 1 and 2.

Figure 3:
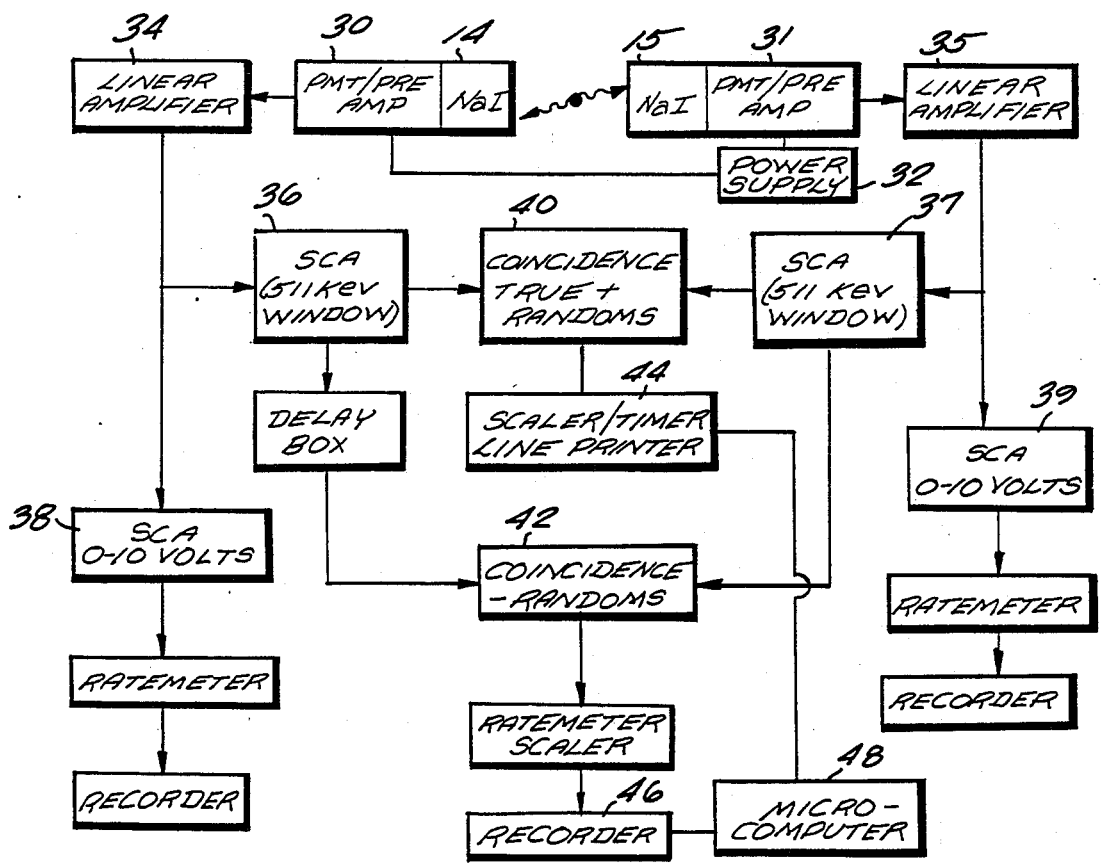
FIG. 3 is a schematic view illustrating exemplary circuitry utilizable in the apparatus of FIG. 1.

The circuitry 20 is connected by cables 28, 29 to the detectors 14, 15, and exemplary circuitry is illustrated schematically in FIG. 3. The circuitry includes a photomultiplier tube/preamplifier 30, 31 operatively connected to each of the detectors 14, 15, respectively, and powered by a power supply 32. The structures 30, 31 are in turn connected to linear amplifiers 34, 35, respectively, with two branches extending from each, a first branch extending to a single channel analyzer and circuitry for correcting for random detections of gamma rays by the detectors, and the second branch extending to a single channel analyzer for merely recording the gross number of detections by the detector. That is amplifier 34 is connected to SCA 36 and to SCA 38. SCA 36 is restricted to approximately a 511 kev window (the energy of the gamma rays), while SCA 38 has a broad range (0.10 volts). SCA 37 is identical to 36, and SCA 39 is identical to 38.

The output from SCAs 36, 37 lead to both circuit components 40 and 42. Circuit component 40 provides a measure of the coincident detections by the detectors 14, 15, plus randoms, and the output thereof passes to component 44. Circuitry component 42 provides for the coincident detection minus the random gamma rays detected by the detectors 14, 15, and the output thereof ultimately can be provided to recorder 46. The output from recorder 46, and additionally from element 44 where desired, is analyzed by microcomputer 48.

Figure 4:
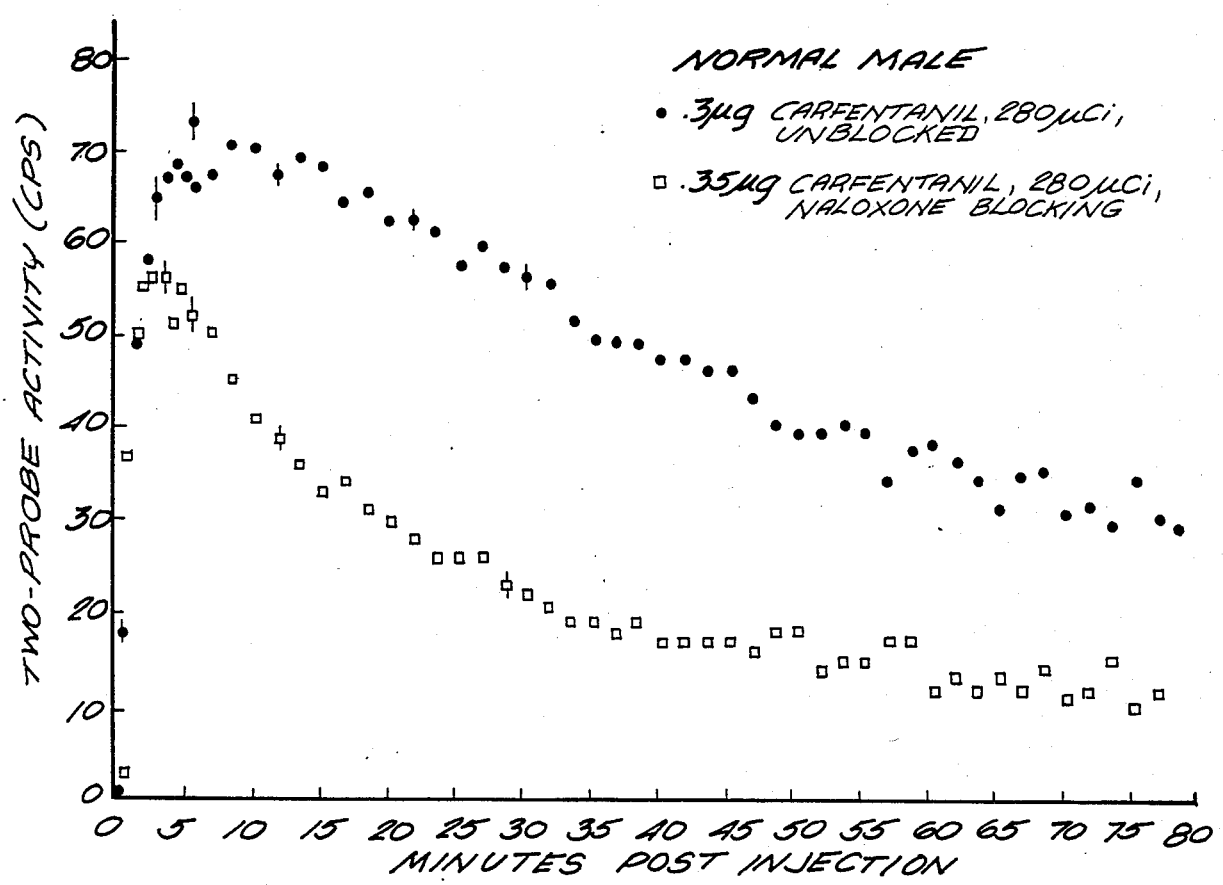
FIG. 4 is a graphical representation of brain monitoring that may be practiced utilizing the apparatus of FIGS. 1 through 3.

FIG. 4 provides a plot of the output from the apparatus of FIGS. 1 through 3 when practicing a particular procedure according to the invention, and demonstrates the utility thereof. FIG. 4 shows the actual plot of a normal male subject for demonstration purposes only. The normal male subject did not have a narcotic overdose, but the narcotic blocking drug Naloxone was administered to him.

The procedures practiced to obtain the results in FIG. 4 were as follows:

The patient was injected with 0.3 micrograms of carbon-11 carfentanil, which is a radioactive tracer substance comprising or consisting of a ligand that binds to opiate receptors. The dark circles illustrated in FIG. 4 show the level of binding of the drug to opiate neuroreceptors in the subject's brain from immediately after injection to approximately 80 minutes after injection. Readings were taken periodically (approximately every 2–3 minutes). The readings were taken by causing the subject to lay his head on a head support 22 between a pair of sodium iodide detectors 14, 15, as illustrated in FIGS. 1 through 3, and the output shown in FIG. 4 was corrected for randoms by the circuitry 20.

After the radioactive tracer disappeared by radioactive decay (the half life of carbon 11, for instance, is 20 minutes), a blocking dose of Naloxone was injected into the subject. Naloxone is typically administered to victims of drug overdose in order to wake them up, and binds to the opiate receptors. After the injection of Naloxone, the subject was then injected with 0.35 micrograms of carbon-11 carfentanil, and measurements taken at approximately the same frequency as for the first injection. The results of the second measurement are indicated by the squares in the graph of FIG. 4. The difference between the top graph and the bottom graph is indicative of the number of opiate neuroreceptors blocked by the Naloxone.

In the broadest concepts of the invention, the first step is to administer a tracer substance comprising or consisting of a ligand that binds to presynaptic or postsynaptic neuroreceptors. Typically the tracer substance will be a radioactive isotope which emits positrons (which combine with an electron to yield two gamma rays that come off in opposite directions), or single photon gamma rays. Carbon 11, fluorine 18, nitrogen 13, and oxygen 15 are preferred radioactive isotopes. The exact form of the radioactive isotope will depend upon whether dopamine, serotonin, opiate, or other neuroreceptors are to be studied; for instance carbon-11 N-methylspiperone is administered if dopamine receptors are to be studied, while carbon-11 carfentanil is administered if opiate receptors are to be studied.

After administering the tracer substance, one waits a period of time sufficient for the ligand to bind to the neuroreceptors, and measures emissions from the tracer substance that are indicative of the number of neuroreceptors and the degree of occupancy or blocking of the neuroreceptors. For instance where a radioactive isotope is the tracer substance, gamma ray emissions will be measured, preferably utilizing the apparatus illustrated in FIGS. 1 through 3. Utilizing the apparatus illustrated in FIGS. 1 through 3, the cost of the measuring device is significantly less than if, for example, a PET scanner were utilized. Also, since PET images require several hundred times more gamma ray photons for their production than does the measurement of the radioactivity within a large volume of tissue (such as the whole brain or frontal lobes), microcuries of radioactive tracer can be detected utilizing the apparatus of FIGS. 1 through 3, rather than millicuries (as where a PET is utilized). Thus there can be up to about a 500 fold decrease in the cost of the radioactive tracer. While the apparatus illustrated in FIGS. 1 through 3 is preferred, however, other mechanisms for measuring emissions from the tracer substance, such as PET scanners, may be utilized.

After the emissions are measured, the number of neuroreceptors and the degree of occupancy or blocking of the neuroreceptors by another drug (besides the tracer substance) are computed utilizing a mathematical model computation, for example. For instance a typical mathematical model computation that can be utilized is described in "Effects of Age on Dopamine and serotonin Receptors Measured by Positron Tomography in the Living Human Brain" by Wong, Wagner, et al, SCIENCE 226:1393-6, Dec. 21, 1984. Such a mathematical model is also described in "Absorbed Fractions for Dose Calculations of Neuroreceptor PET Studies" by Bice, Wagner, et al. The disclosures of these texts are hereby incorporated by reference herein.

The calculations achieved in the preceding step are compared with an intra-person or inter-person control to determine the degree drug response. Where an intra-person control is available, of course it should be utilized since it is more accurate. However inter-person controls can be developed that are fairly accurate, given the age, sex, and like characteristics of the patient, and may be utilized where an intra-person control cannot be obtained due to the circumstances. Based upon the comparison made, then, one can gauge the further treatment of the patient with drugs to optimize the drug treatment of the patient.

Two specific examples of the practice of the an exemplary method according to the present invention will now be set forth, the examples particularly directed to treatment of a patient having schizophrenia, and treatment of a patient having a drug addiction. However it is to be understood that these examples are only illustrative, and the invention is applicable to the treatment of other nervous and mental diseases, or other aspects of drug addition.

In a first exemplary procedure, a living patient having schizophrenia is treated as follows: The patient injected with carbon-11 N-methylspiperone. The patient lays down with his head on the head rest 22, and continuous or intermittent measurements of the gamma rays emitted by the radioactive drug are taken utilizing the apparatus in FIGS. 1 and 2. Measurement is taken from the approximate time of injection until approximately 60 minutes has elapsed. The measurements are plotted on a graph (as illustrated in FIG. 4), or otherwise stored or analyzed.

A delay of a sufficient period of time is then occasioned so that the carbon-11 has disappeared by radioactive decay. Since the half life of carbon-11 is 20 minutes, a delay of approximately two hours is usually sufficient. Then the patient is injected with a neuroleptic drug, such as Haloperidol, in non-radioactive form. The injection of Haloperidol is at a dosage deemed sufficient to provide effective blocking of the dopamine neuroreceptors. Then the patient is again given an injection of carbon-11 N-methylspiperone, and the gamma ray emissions again measured, with the results of those measurements plotted (as illustrated in FIG. 4), or otherwise recorded or analyzed. A comparison of the measurements from the first and second injections of N-methylspiperone provides an indication of the degree of blockade of the dopamine neuroreceptors by the dose of Haloperidol administered, and thus the effectiveness of the dose can be determined. The dosage to be commonly administered to the patient for the treatment of his schizophrenia may then be adjusted depending upon the effectiveness of the dose given.

In a second exemplary procedure, a patient who takes methadone for a narcotic drug addiction is injected with carbon-11 carfentanil, which binds to opiate neuroreceptors. Measurements of the gamma rays emitted from the patient's brain are taken, utilizing the apparatus of FIGS. 1 through 3, for a period of about 60 minutes after injection. After the radioactive tracer has disappeared by radioactive decay, an opiate receptor blocking drug, such as Naltrexone, is administered in non-radioactive form, and then injection with carbon-11 carfentanil is repeated, and measurements from the second injection also taken. The measurements from the first and second injections of carfentanil are then compared to determine the degree of blockage that occurred from the administration of the predetermined dose of Naltrexone. This then determines whether the dose of Naltrexone administered is sufficient to prevent withdrawal, and to take the place of methadone in subsequent treatment of the patient.

It will thus be seen that according to the present invention a method and apparatus have been provided for technologically and cost-effectively monitoring the effectiveness of drugs and substances that affect brain chemistry. While the invention has been herein shown and described in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to emcompass all equivalent structures and methods.

What is claimed is:

1. Apparatus for monitoring the effectiveness of drugs and substances that affect brain chemistry comprising:

a support structure for supporting a living patient in a supine position, including a head support structure;

first and second gamma ray directional detectors;

means for mounting said first and second gamma ray directional detectors so that they are operatively disposed on opposite sides of said head support for receiving gamma rays emitted from the head of a patient supported by said patient support;

circuitry means operatively connected to said gamma ray detectors for facilitating determination of the gamma ray as detected by said detectors, said circuitry means including a photomultiplier tube/- preamplifier operatively coupled to each of said detectors, respectively, a linear amplifier operatively coupled to each said preamplifier, each said linear amplifier having first and second branches extending therefrom, a first branch of each said linear amplifier extending to a single channel analyzer and to means for correcting random detections of gamma rays by the detectors, said second branch of each said linear amplifier being operatively coupled to a single channel analyzer for recording the gross number of detections by the detector, each said single channel analyzer for recording the gross number of detections being operatively coupled to a means for providing a measure of the coincident detections by the detectors plus randoms and further each said single channel analyzer for recording the gross number being operatively coupled to means for providing the coincident detection minus the random gamma rays detected by the detectors, means for coupling the output of each said means for providing to a means for determining therefrom the number of neuroreceptors and the degree of occupancy or blocking and for comparing the same with an intraperson or interperson control to determine the degree of drug response so that the effectiveness of drugs and other substances on brain chemistry may be assessed.

2. Apparatus as recited in claim 1 wherein said gamma ray detectors are selected from the group consisting of NaI and BiGe detectors.

3. Apparatus as recited in claim 2 wherein said mounting means comprises a collimator of lead upstanding from said support structure on either side of said head support, a gamma ray detector disposed within each lead collimator.

* * * * *

UNITED STATES PATENT AND TRADEMARK OFFICE
CERTIFICATE OF CORRECTION

PATENT NO. : 4,772,791
DATED : September 20, 1988
INVENTOR(S) : WAGNER

It is certified that error appears in the above-indentified patent and that said Letters Patent is hereby corrected as shown below:

In Column 1, after line 5, the following paragraph should be added:

--The invention described herein was made in the course of work under grant or award from the U.S. Department of Health and Human Services.--

Signed and Sealed this

Twenty-fifth Day of April, 1995

Attest:

BRUCE LEHMAN

Attesting Officer          Commissioner of Patents and Trademarks